Nov. 1, 1949. S. POULSEN Plant Pat. 889
ROSE PLANT
Filed July 22, 1948
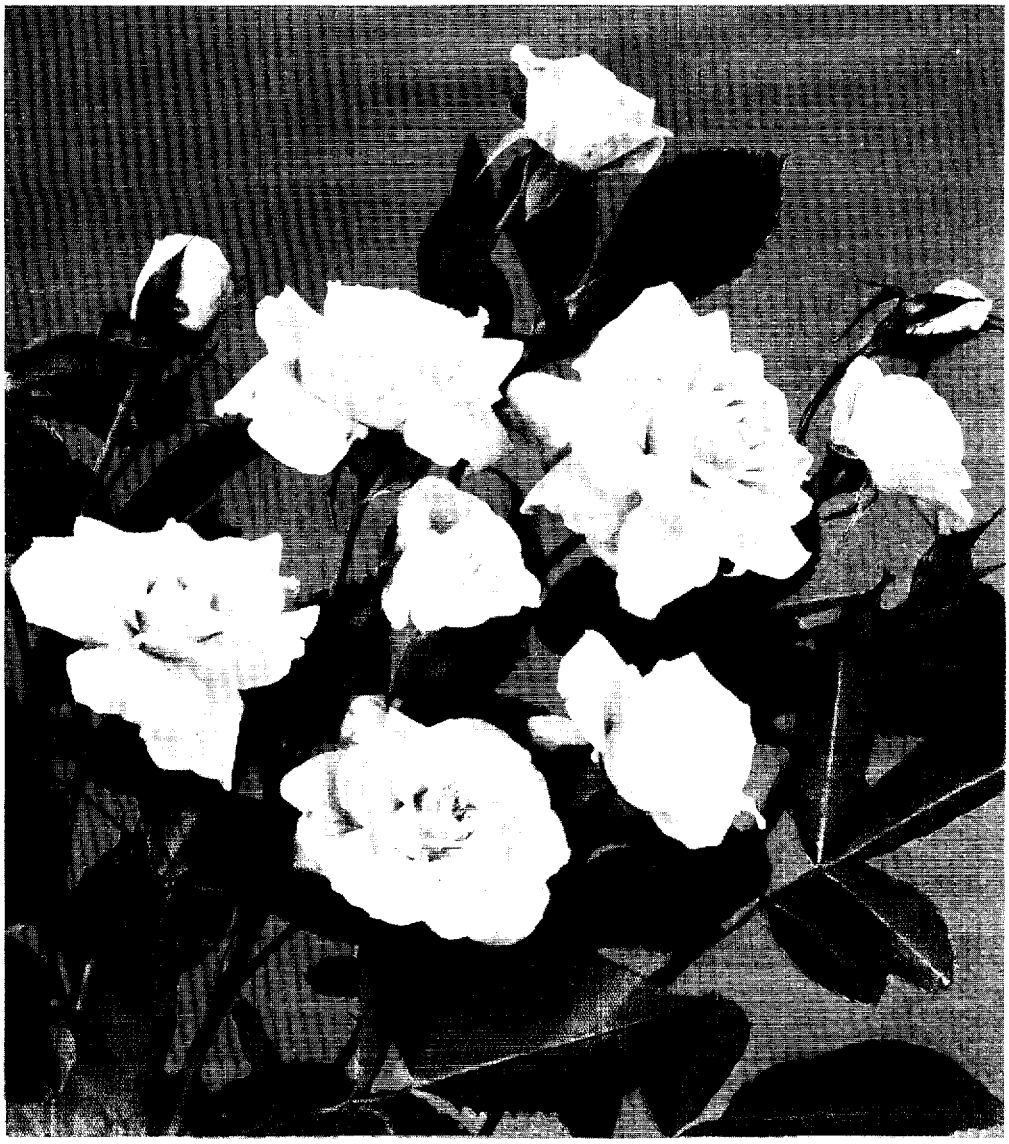
Inventor
Svend Poulsen
By Robb & Robb
Attorneys

UNITED STATES PATENT OFFICE

889

ROSE PLANT

Svend Poulsen, Copenhagen, Denmark, assignor to The Conard-Pyle Corporation, West Grove, Pa., a corporation of Pennsylvania Application July 22, 1948, Serial No. 40,069

1 Claim. (Cl. 47—61)

The present invention relates to a new and distinct variety of rose plant of the hybrid polyantha class characterized as to novelty dominantly by its adaptability for both cut-flowers and garden decoration, by the purity of the color of its flowers and their excellent form and large size for varieties of this class, combined with its exceptionally vigorous growing habit over a long blooming period and extraordinary freedom of flowering.

Asexual reproduction shows that these characteristics hold true through succeeding propagations.

In the drawing are shown specimens of this new variety, illustrating the flowers at different stages of development from bud to full blown blossoms, together with specimens of young and mature foliage.

The following is a detailed description of the new variety, all references to color being in accordance with Ridgway's Color Standards and Nomenclature, and ordinary dictionary definition.

Type: Hardy; bush; for cut flowers and garden decoration.

Class: Hybrid polyantha.

Breeding: Seedling.

*Seed parent.*—A seedling of "Mrs. Cutbush."

*Pollen parent.*—"Edina."

Propagation: Holds its distinguishing characteristics through succeeding propagations by budding.

*Flower*

Locality where grown: West Grove, Pennsylvania.

Flowers borne: Several to stem in cluster, on normal, medium long stems.

Quantity of bloom: Abundant outdoors and in greenhouse.

Continuity: Continuous.

Fragrance: Slight to moderate; old China rose fragrance.

Bud:

*Peduncle.*—Long; slender; erect; medium green; medium rough; numerous minute red prickles.

*Before calyx breaks.*—Size—Medium. Form—pointed; with foliaceous appendages on the surface of the bud; with slender, entire foliaceous parts extending beyond the tip of the bud equal to one-half or more of its length.

*As calyx breaks.*—Color—White.

*As first petal opens.*—Size—Medium small.

Form—elliptical, pointed. Color—white (sometimes faint blush). Outside: White flushed Light Viridine Yellow, Plate V, at base; inside: White delicately veined Light Viridine Yellow to Pale Viridine Yellow, Plate V.

*Opening.*—Opens up well.

Bloom: Size, when fully open—large; 3 inches to 3¼ inches.

*Petalage.*—Double; 30 to 50 or more petals; arranged regularly with petaloids in center.

*Form.*—Cupped at first; becoming open cupped; petals remaining at first loosely cupped, outer row of petals first, rolled outward; becoming later, at maturity, loosely cupped.

Petals: Firm and silky; with inside like white silk crepe and outside more shiny.

*Shape.*—Outside—rounded heart shape; scalloped with one notch usually, sometimes a compound notch. Intermediate—obovate; emarginate scalloped with one notch; less deeply notched than outside petals. Inside—elongated heart shape, scalloped with one notch, with some irregular petaloids.

This description of a newly opened flower was made from a rose grown in a greenhouse in the month of March at West Grove, Pa.

*Color.—Outside petal.*—outside surface: White with trace of Martius Yellow, Plate IV, at base, variable with angle of light; inside surface: same as outside surface. *Intermediate petal* — outside surface: White with trace of Martius Yellow, Plate IV, at base, variable with angle of light; inside surface: same as outside surface. *Inner petal*—outside surface: White with trace of Martius Yellow, Plate IV, at base, variable with angle of light; inside surface: same as outside surface.

This description was made from a rose that was open for three days in a greenhouse in the month of March, at West Grove, Pa.

*Color.—Outside petal.*—outside surface: White with faint trace of Martius Yellow, Plate IV, at base of petals, variable with angle of light; inside surface: same as outside surface. *Inside petal*—outside surface: White with faint trace of Martius Yellow, Plate IV, at base of petals, variable with angle of light; inside surface: same as outside surface.

*General color effect.*—Newly opened flower—White with luminous glow. Three days open—White with faint luminous glow at center.

*Behavior.*—Drop off cleanly.

*Flower longevity.*—On bush in greenhouse—10 to 14 days in March. Cut roses grown in greenhouse kept at living room temperature—5 to 6 days in March.

*Reproductive organs*

Stamens: Many; arranged irregularly about pistils, mixed with petaloids.

Filaments: Medium length; yellow; most with anthers.

Anthers: Small; yellow-brown.

Pistils: Medium number.

Styles: Even; medium long; medium heavy; loosely bunched.

Stigma: Pale yellow green.

Ovaries: All enclosed in calyx.

Sepals: Moderately long; recurved; many curled. *Color*—Biscay Green (Plate XVII), sometimes lined or touched variably with Sorghum Brown (Plate XXXIX) at tip.

*Plant*

Foliage:

*Leaves.*—Compound of seven leaflets; abundant; medium size; moderately glossy.

*Leaflets.*—Shape — rounded obovate with apex obtuse; base rounded obtuse; margin serrate.

*Color.*—Mature—upper surface: Yew Green, Plate XXXI; under surface: Jade Green, Plate XXXI. *Young*—upper surface: Cress Green, Plate XXXI; under surface—Light Cress Green, Plate XXXI.

*Rachis.*—Medium heavy. Upper side—minutely prickly; under side—sparsely thorny.

*Stipules.*—Long; narrow; with medium long points, turning out at varying angles of less than 45° or about; finely serrate.

*Disease.*—Resistant.

Growth:

*Habit.*—Bushy; upright; branched.

*Growth.*—Vigorous.

*Canes.*—Medium heavy.

*Main stems.*—Bright green. *Thorns*—several; long; hooked downward; with long, narrow base. *Prickles and hairs*—none.

*Branches.*—Bright green. *Thorns*—Few to several; medium long; hooked downward; with narrow base. *Prickles and hairs*—none.

*New shoots.*—Bright green. *Thorns, prickles, and hairs*—none.

I claim:

A new and distinct variety of rose plant of the hybrid polyantha class, characterized as to novelty by its adaptability for use as cut-flowers and garden decoration; its exceptionally vigorous growing habit over a long blooming period; the extraordinary freedom of flowering; the purity of the color of its flowers, and the excellent form and large size of said flowers, substantially as shown and described.

SVEND POULSEN.

No references cited.